US012083352B2

(12) United States Patent
Apperson et al.

(10) Patent No.: US 12,083,352 B2
(45) Date of Patent: Sep. 10, 2024

(54) BATTERY MANAGEMENT FOR MEDICAL DEVICE

(71) Applicant: Physio-Control, Inc., Redmond, WA (US)

(72) Inventors: Ryan W. Apperson, Bothell, WA (US); Mark Rutzer, Seattle, WA (US); Rockland W. Nordness, Kirkland, WA (US); Kristina Edmonson, Woodinville, WA (US); Chad Bartlett, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 483 days.

(21) Appl. No.: 17/507,225

(22) Filed: Oct. 21, 2021

(65) Prior Publication Data

US 2022/0193432 A1 Jun. 23, 2022

Related U.S. Application Data

(60) Provisional application No. 63/127,459, filed on Dec. 18, 2020.

(51) Int. Cl.
*A61N 1/39* (2006.01)
*H02J 7/00* (2006.01)

(52) U.S. Cl.
CPC ......... *A61N 1/3981* (2013.01); *A61N 1/3937* (2013.01); *H02J 7/0024* (2013.01); *H02J 7/0048* (2020.01); *H02J 7/0044* (2013.01)

(58) Field of Classification Search
CPC .... A61N 1/3981; A61N 1/3937; A61N 1/378; A61N 1/3904; A61N 1/3975; A61N 1/3925
See application file for complete search history.

(56) References Cited

U.S. PATENT DOCUMENTS

| 5,285,779 | A | 2/1994 | Cameron et al. |
| 6,223,077 | B1 | 4/2001 | Schweizer et al. |
| 6,955,864 | B1 | 10/2005 | Vaisnys et al. |
| 7,625,662 | B2 | 12/2009 | Vaisnys et al. |
| 7,813,800 | B2 | 10/2010 | Fleenor et al. |
| 7,855,010 | B2 | 12/2010 | Vaisnys et al. |

(Continued)

FOREIGN PATENT DOCUMENTS

| EP | 2478935 A2 | 7/2012 |
| EP | 2478935 A3 | 10/2012 |

OTHER PUBLICATIONS

European Search Report for related European Patent Application No. 21215110.4 mailed May 11, 2022.

*Primary Examiner* — Brian T Gedeon
(74) *Attorney, Agent, or Firm* — McDonnell Boehnen Hulbert & Berghoff LLP (57) ABSTRACT

The present disclosure relates generally to a defibrillator assembly comprising a defibrillator having a first operating mode for delivering a high energy output to a patient and a second operating mode for monitoring the patient, a first battery unit operably coupled to the defibrillator, and a second battery unit operably coupled to the defibrillator. One of the first battery unit and the second battery unit provides power to the defibrillator during the second operating mode. Both the first battery unit and the second battery unit provide power to the defibrillator during the first operating mode.

15 Claims, 5 Drawing Sheets

(56) References Cited

U.S. PATENT DOCUMENTS

| | | |
|---|---|---|
| 8,564,242 B2 | 10/2013 | Hansford et al. |
| 8,564,447 B2 | 10/2013 | Trock et al. |
| 9,142,992 B2 | 9/2015 | Malackowski et al. |
| 9,174,060 B2 | 11/2015 | Kameli |
| 9,419,462 B2 | 8/2016 | Sollanek |
| 9,757,578 B2 | 9/2017 | Lu et al. |
| 9,811,133 B2 | 11/2017 | Cudak et al. |
| 9,827,435 B2 | 11/2017 | Walker et al. |
| 10,029,109 B2 | 7/2018 | Beyer et al. |
| 10,071,256 B2 | 9/2018 | Montgomery et al. |
| 10,425,894 B2 | 9/2019 | Howell et al. |
| 10,677,853 B2 | 6/2020 | Laughery et al. |
| 10,694,463 B2 | 6/2020 | Howell et al. |
| 2012/0150247 A1 | 6/2012 | Meier et al. |
| 2016/0067510 A1 | 3/2016 | Norton et al. |
| 2016/0121131 A1* | 5/2016 | Delise ............... A61N 1/3975 607/5 |
| 2018/0161587 A1 | 6/2018 | Beyer et al. |

* cited by examiner

BATTERY MANAGEMENT FOR MEDICAL DEVICE

CROSS-REFERENCE TO RELATED APPLICATIONS

The present application claims priority to U.S. provisional application No. 63/127,459, filed on Dec. 18, 2020, the entire contents of which are herein incorporated by reference.

BACKGROUND OF THE DISCLOSURE

There are a number of medical devices that utilize one or more battery units to provide power thereto. Over time and/or repeated charge cycles, the health of the battery units can deteriorate. Deteriorating battery health can reduce the effectiveness of the medical device, and potentially result in a failure.

One example medical device is an external defibrillator. An external defibrillator uses power from a battery unit to apply a current through the tissue of a patient. This operation can require drawing a high level of power from the battery unit over a short period of time. Management of battery life is useful for external defibrillators. They are typically used by first responders or laypersons in the field, where alternative sources of power for powering the device or recharging batteries are not readily available, they can rely on battery power for providing support for cardiopulmonary resuscitation (CPR) (e.g., timing, alarms, rate and depth monitors), for monitoring of patients to determine whether and when a shock is appropriate (e.g., ECG, $SpO_2$, $CO_2$, temperature and blood pressure), and for transmitting patient information via cellular data to hospitals so that Emergency Rooms can be prepared with appropriate treatment teams and equipment.

When a defibrillator or a user of the defibrillator determines that a shock is appropriate, the defibrillator delivers a high energy shock (e.g., 200 joules or more) to the patient. The ability to support CPR and perform these defibrillation functions in the field can reduce the risk of death, specifically of patients experiencing cardiac arrest. Further, delay in defibrillation after cardiac arrest begins can decrease the effectiveness of the defibrillation.

Some medical devices have two or more battery units so as to provide backup power. During operation, the medical device can draw power from a first battery until the charge of the first battery is depleted. Then the medical device can draw power from a second battery.

SUMMARY OF THE DISCLOSURE

Within examples described herein, systems and methods are described that manage a first battery unit and a second battery unit of a medical device such that both the first battery unit and the second battery unit power the medical device in a first operating mode, and only one of the first battery unit or the second battery unit power the medical device in a second operating mode.

Within additional examples described herein, the systems and methods described above additionally monitor the remaining charge of a first battery unit and a second battery unit of a medical device and adjust the operation of the medical device based on the remaining charge of the first battery unit and the second battery unit.

Within additional examples described herein, the systems and methods described above additionally monitor the remaining useful life of a first battery unit and a second battery unit of a medical device and adjust the operation of the medical device based on the remaining useful life of the first battery unit and the second battery unit.

Additional aspects of the disclosure will be evident from the disclosure herein.

BRIEF DESCRIPTION OF THE DRAWINGS

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more implementations of the disclosure, and together with the description serve to explain the principles and operation of the disclosure.

DETAILED DESCRIPTION

The present disclosure provides for systems and methods for battery management of a device, such as a medical device. Within examples, the system can include a medical device having a first battery unit and a first operating mode or high power operating mode in which power is drawn from the first battery unit at a relatively high rate. The system further includes a controller for monitoring at least one condition of the first battery unit, such as remaining charge and/or remaining useful life, and adjusting operation of the device based on the at least one monitored condition.

In some examples, the device has a second battery unit. The controller monitors the same one or more conditions of the second battery unit as is monitored for the first battery unit. The monitored conditions are compared to each other and/or to predetermined threshold values. Operation of the device is adjusted based on this comparison.

The device draws power from both battery units simultaneously under certain conditions, such as when charging a defibrillator capacitor, in order to achieve faster charge times. Additionally, the device draws power from both battery units when both battery units are below a threshold value for remaining charge or below a threshold value for remaining useful life so that the device remains operation for a longer period of time.

The device allows for sharing device load between the two battery units. Sometimes the device load is shared evenly between the battery units. Other times the device load is shared unevenly by a predetermined value, e.g., 70%-30%, or proportional to the remaining charge of the respective battery units.

Additionally or alternatively, the device has a second operating mode or a low power operating mode.

Figure 1:
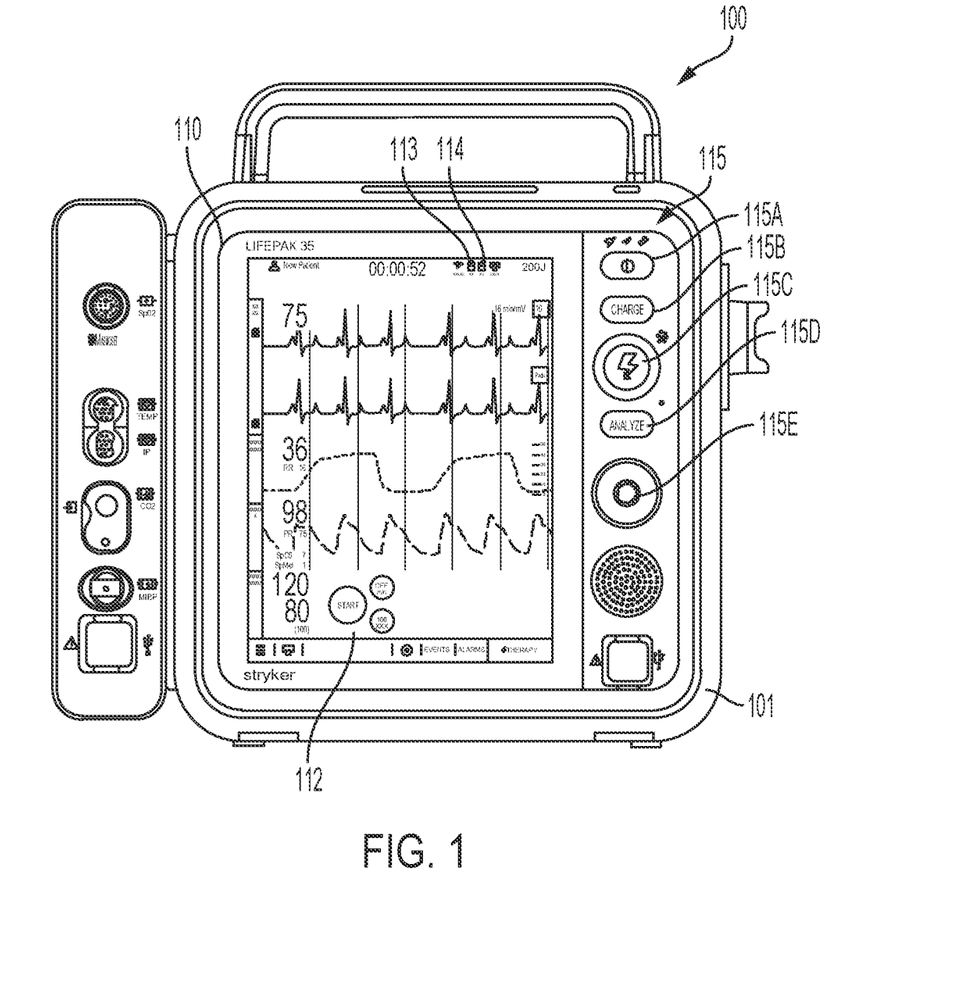
FIG. 1 is a front view of a medical device, according to an example implementation.
Figure 2:
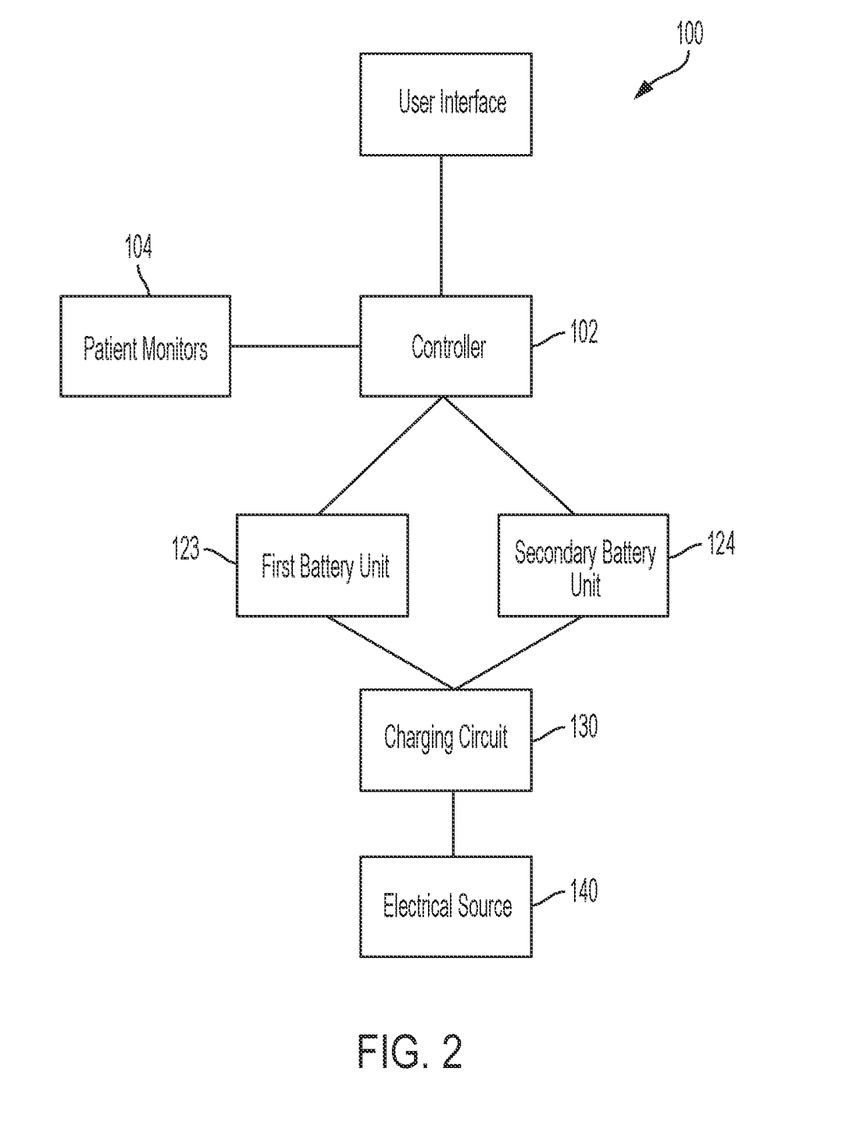
FIG. 2 is a simplified block diagram of the medical device of FIG. 1.

An example medical device 100 is illustrated in FIGS. 1-2. The medical device 100 is an external defibrillator assembly, and can be one of multiple different types, each with different sets of features and capabilities. As one example, the medical device 100 can be an automated external defibrillator (AED), such as a public access defibrillator AED. An AED can make a decision as to whether or not to deliver a shock to a patient automatically. For example, an AED can sense physiological conditions, such as shockable heart rhythms, of a patient via therapy pads applied to the patient, and make the decision based on an analysis of the patient's heart. Further, an AED can either deliver the shock automatically, or instruct a user to deliver a shock, e.g., by pushing a button. AEDs can be operated by medical professionals as well as people who are not in the medical profession, such as policemen, firemen, or even a person with first-aid and CPR/AED training. AEDs can be located in public spaces or homes so that lifesaving treatment can hopefully be initiated before medical professionals arrive.

As another example, the medical device 100 can be a more advanced device, such as a monitor defibrillator. Monitor defibrillators are intended to be used by trained medical professionals, such as doctors, nurses, paramedics, emergency medical technicians, etc. As the name suggests, a monitor defibrillator is a combination of a monitor and a defibrillator. As a defibrillator, a monitor defibrillator can be one of different varieties, or even versatile enough to be able to switch among different modes that individually correspond to the varieties. One variety is that of an automated defibrillator, which can determine whether a shock is needed and, if so, charge to a predetermined energy level and instruct the user to deliver the shock. Another variety is that of a manual defibrillator, where the user determines the need and controls delivery of the shock. As a patient monitor, the monitor defibrillator has features additional to what is needed for operation as a defibrillator. These features can be for monitoring physiological indicators of a patient in an emergency scenario, for instance.

As shown in FIG. 1, the medical device 100 has a main body 101 with a user interface 110 provided thereon. The user interface 110 includes a screen 112 for displaying information to the user, such as patient information. The user interface further includes a first battery unit indicator 113 and a second battery unit indicator 114. The first battery unit indicator 113 and second battery unit indicator 114 display a status of a first battery unit 123 and second battery unit 124 (see FIG. 2), respectively.

The user interface 110 additionally includes controls 115. The controls 115 include a series of buttons 115A-115E for operating the medical device 100. The first button 115A is a power button for powering the medical device 100 on and off.

The second and third buttons 115B and 115C, respectively, are for operating the medical device 100 in a first mode of operation. The first mode of operation is a high power mode of operation. In this mode, the medical device 100 delivers a high energy output to a patient. For example, a high energy output into the tissue of the patient.

The second button 115B is a charge button. Pressing the second button 115B causes a charging circuit 130 to charge an electrical source 140 with power from one or both of the first battery unit 123 and the second battery unit 124.

The third button 115C is a discharge button. Pressing the third button 115C causes the medical device 100 to discharge power from the electrical source 140 into the patient.

The fourth button 115D is for operating the medical device 100 in a second mode of operation. The second mode of operation is a lower power mode of operation. In this mode, the medical device 100 monitors physiological indicators of a patient. In some examples, the medical device 100 monitors electrical activity of a patient's heart and generates an electrocardiogram ("ECG"). In addition, the medical device can analyze the electrical activity of the patient's heart, and make a decision as to whether or not to deliver a shock to a patient. For instance, upon identifying a shockable rhythm the medical device can cause the screen 112 to provide a message that instructs a user to deliver an electric shock. The screen 112 can also provide other messages that recommend other therapy, such as a recommendation to provide cardiopulmonary resuscitation (CPR). During the second operating mode, the medical device 100 is powered by only one of the first battery unit 123 or second battery unit 124.

The fifth button 115E is used for navigating through displayed information on the user interface 110. By navigating through menus using the fifth button 115E, additional operations can be performed. Alternatively or additionally, operating parameters can be manually adjusted.

As shown in FIG. 2, the medical device 100 includes a controller 102 operably coupled to the user interface 110, patient monitors 104, the first battery unit 123, the second battery unit 124, the charging circuit 130, and the electrical source 140. In some implementations, the controller 102 includes a computing device, such as a processor, and computer readable memory. The computer readable memory stores executable instructions which, when executed by the processor cause the medical device 100 to perform any of the methods and operations described herein. In some forms, the controller 102 is divided into multiple processors or computing devices. For example, the controller 102 can include one processor that operates the charging circuit 130 and the electrical source 140 and a second processor that operates the patient monitors 104.

The electrical source 140 is configured to store a high power charge for a short period of time. For instance, the electrical source 140 can be configured to store electrical energy in the form of an electrical charge, when preparing for delivery of a shock. The medical device 100 can further include a discharge circuit (not shown), which can be controlled to permit the energy stored in the electrical source 140 to be discharged to defibrillation pads of a therapy cable. Controller 102 can instruct the discharge circuit to output a shock using one of various energy levels. The energy levels can range from 50 Joules to 360 Joules. In some examples, the electrical source comprises one or more capacitors.

The first battery unit 123 is a power storage device having one or more power cells. In some examples, the first battery unit 123 is a lithium battery, alkaline battery, or other type of standard battery. Alternatively, the first battery unit 123 includes one or more high capacity capacitors, such as supercapacitors. Similarly, the second battery unit 124 includes one or more power cells. The second battery unit is a lithium battery, alkaline battery, high capacity capacitor, or other standard power storage device.

The first battery unit 123 and second battery unit 124 are rechargeable. In some forms, the medical device 100 includes a charging cable or port for receiving a charging cable such that the medical device 100 can be electrically coupled to an external power source. The external power source charges the first battery unit 123 and/or second battery unit 124 while the first and second battery units 123/124 are coupled to the medical device 100. Alternatively or additionally, the first battery unit 123 and second battery unit 124 are each detachably coupled to the medical device 100 so as to enable a user to replace a defective or low charge battery unit with an additional battery unit. In some forms, the detached first battery unit 123 and second battery unit 124 can be coupled to a battery charger to recharge.

The first battery unit 123 and second battery unit 124 are selectively coupled to the electrical source 140 by the charging circuit 130. Both the first battery unit 123 and the second battery unit 124 are operably coupled to the electrical source 140 so as to be usable to charge the electrical source 140 while the medical device in a first mode of operation. The first battery unit 123 and second battery unit 124 are also operably coupled to the user interface 110 and patient monitors 104 so as to provide power thereto while the medical device 100 is in a second mode of operation.

The controller 102 monitors parameters of the first battery unit 123 and the second battery unit 124. The controller 102 measures the remaining charge of both the first battery unit 123 and the second battery unit 124. The remaining charges of the first battery unit 123 and second battery unit 124 are displayed to the user by the indicators 113 and 114 discussed above.

In some forms, the controller 102 includes a battery charge monitor to monitor the maximum charge of the first battery unit 123 and the second battery unit 124. Over a number of charge cycles, the maximum charge achievable by the first battery unit 123 and second battery unit 124 lessens compared to the original maximum charge. The battery unit indicators 113, 114 indicate the current charge of the battery units 123, 124 relative to the current maximum charge thereof. In alternative implementations, the battery unit indicators 113, 114 indicate the remaining charge as an estimated run time remaining, as opposed to or in addition to a percentage of maximum charge.

The controller 102 further monitors the remaining useful life of the first battery unit 123 and the second battery unit 124. The remaining useful life is determined based on one or more parameters of the first battery unit 123 and the second battery unit 124. For example, the controller 102 determines the remaining useful life of a battery unit based on absolute state of charge, battery current, battery voltage, charging current, charging voltage, discharge cycle count, date of battery first use, full charge capacity, relative state of charge, remaining capacity, run time to empty, temperature, or combinations thereof. In one example, the controller 102 determines the remaining useful life of a battery unit by monitoring the full charge capacity of the battery unit compared to an original full charge capacity. Alternatively or additionally, the controller 102 determines the remaining useful life by monitoring the temperature of the battery unit and the cycle count of the battery unit. In some forms, the controller 102 determines the remaining useful life of the first battery unit 123 and second battery unit 124 indirectly by receiving an indication of remaining useful life from a sub-controller or other firmware of the first battery unit 123 or the second battery unit 124.

In operation, the controller 102 adjusts operation of the medical device 100 based on the monitored battery parameters. In some examples, the controller 102 compares the remaining charges of the first battery unit 123 and the second battery unit 124. While the medical device is in the second operating mode, the controller 102 uses power from only one of the first battery unit 123 or the second battery unit 124. In some forms, the controller 102 uses power from the one of the first battery unit 123 or the second battery unit 124 having the lower remaining charge. Drawing power from the battery unit having the lower remaining charge during the second mode of operation reserves the power of the battery unit having the higher remaining charge. In this way, a single battery unit is reduced to a replacement level charge at a time, and a user can keep the medical device 100 operational by replacing the battery unit with a single backup battery unit.

Alternatively or additionally, the controller 102 compares the remaining charges of the first battery unit 123 and the second battery unit 124 to a first remaining charge threshold and a second remaining charge threshold, respectively. The remaining charge thresholds can represent a level of remaining charge at which the respective battery unit should be replaced or recharged. In some forms, the first remaining charge threshold and the second remaining charge threshold are equal. In one example, the threshold value is approximately 25% of the total charge capacity.

When both the first battery unit 123 and the second battery unit 124 have remaining charges above the threshold values, the controller 102 uses power from the battery unit having the lower remaining charge while in the second operating mode, as discussed above.

When one of the first battery unit 123 or the second battery unit 124 has a remaining charge equal to or below the threshold value and the other of the first battery unit 123 or the second battery unit 124 has a remaining charge above the threshold value, the battery unit having the higher remaining charge is used while the medical device 100 is in the second operating mode.

When both the first battery unit 123 and the second battery unit 124 have remaining charges below the respective threshold values, both battery units are used while the medical device 100 is in the second operating mode.

In alternative implementations, the one of the first battery unit 123 and the second battery unit 124 having the higher remaining charge is used to provide power to the medical device 100 while in the second operating mode.

In some examples, both the first battery unit 123 and the second battery unit 124 are used to charge the electrical source 140 while the medical device 100 is in the first operating mode. Alternatively, when only one of the first battery unit 123 or the second battery unit 124 has a remaining charge below the respective threshold value, only the other of the first battery unit 123 or the second battery unit 124 is used to charge the electrical source 140 during the first operating mode.

Accordingly, when the remaining charge of the first battery unit 123 is above the first threshold value and the remaining charge of the second battery unit 124 is above the second threshold value, both battery units provide power to the medical device during the first operating mode. When the remaining charge of the first battery unit 123 is below the first threshold value and the remaining charge of the second battery unit 124 is below the second threshold value, both battery units provide power to the medical device during the first operating mode. When the remaining charge of the first battery unit 123 is above the first threshold value and the remaining charge of the second battery unit 124 is below the second threshold value, only the first battery unit provides power to the medical device during the first operating mode. When the remaining charge of the first battery unit 123 is below the first threshold value and the remaining charge of the second battery unit 124 is above the second threshold value, only the second battery unit provides power to the medical device during the first operating mode.

In some forms, power is drawn from the first battery unit 123 and the second battery unit 124 equally while the medical device 100 is in the first operating mode. In alternative forms, the charging circuit 130 draws power from the first battery unit 123 and the second battery unit 124 at rates proportional to their respective charges while charging the electrical source 140 during the first operating mode. In one example, the battery unit having a higher remaining charge provides 70% of the power and the battery unit having the lower remaining charge provides 30% of the power.

The controller 102 can further adjust operation of the medical device 100 based on the remaining useful life of the first battery unit 123 and the second battery unit 124. For example, the controller 102 can compare the remaining useful life of the first battery unit 123 to the remaining useful life of the second battery unit 124. During the second operating mode, the one of the first battery unit 123 and the second battery unit 124 having the longer remaining useful life can be used to power the medical device 100.

Alternatively or additionally, the controller 102 compares the remaining useful life of the first battery unit 123 and the remaining useful life of the second battery unit 124 to a stored first remaining useful life threshold and a stored second remaining useful life threshold, respectively. In some forms, the first remaining useful life threshold and the second remaining useful life threshold are the same threshold. When the first battery unit 123 has a remaining useful life below the first remaining useful life threshold, the controller 102 indicates to a user to replace the first battery unit 123 using the first battery unit indicator 113. When the second battery unit 124 has a remaining useful life below the second remaining useful life threshold, the controller 102 indicates to a user to replace the second battery unit 124 using the second battery unit indicator 114.

When only one of the first battery unit 123 and the second battery unit 124 has a remaining useful life below the threshold value, the controller 102 uses the one of the first battery unit 123 and the second battery unit 124 having the longer remaining useful life (i.e., a remaining useful life above the threshold value) to power the medical device while in the second operating mode.

In some examples, both parameters are used by the controller 102 to control operation of the medical device 100 while in the second operating mode. For instance, while both the first battery unit 123 and the second battery unit 124 have a remaining useful life above the respective threshold value, the controller 102 provides power to the medical device from one or both battery units 123, 124 based on remaining charge, as described above. However, when one of the first battery unit 123 or the second battery unit 124 has a remaining useful life below the threshold value, the battery unit having the longer remaining useful life is used to power the medical device 100.

During the first operating mode, the charging circuit 130 draws power from the first battery unit 123 at a first rate and draws power from the second battery unit 124 at a second rate to charge the electrical source 140. As discussed above, the controller 102 can alter the first rate and the second rate based on the relative remaining charges of the first battery unit 123 and the second battery unit 124. Alternatively or additionally, the controller adjusts the first rate and the second rate based on the remaining useful life of the first battery unit 123 and the remaining useful life of the second battery unit 124, respectively. The first rate is reduced when the remaining useful life of the first battery unit 123 is below the threshold value. Similarly, the second rate is reduced when the remaining useful life of the second battery unit 124 is below the threshold value.

In some examples, the controller 102 controls a maximum first rate and a maximum second rate. The first rate is adjustable, but cannot exceed the maximum first rate. Similarly, the second rate is adjustable but cannot exceed the maximum second rate. In operation, the controller 102 reduces the maximum first rate based on the remaining useful life of the first battery unit 123 and the maximum second rate based on the remaining useful life of the second battery unit 124. For example, the maximum first rate is reduced when the remaining useful life of the first battery unit 123 is below the threshold value and the maximum second rate is reduced when the remaining useful life of the second battery unit 124 is below the threshold value.

In some forms, when one of the first battery unit 123 or the second battery unit 124 has a remaining life below the respective threshold value, the rate at which power is drawn from the other of the first battery unit 123 or the second battery unit 124 during the first operating mode is increased. For example, instead of drawing power 50-50 from the two battery units, the charging circuit draws 70% of its power from the battery unit having the longer remaining life and 30% from the battery unit having the shorter remaining life. Accordingly, the total power drawn from both the first battery unit 123 and the second battery unit 124 remains constant so long as at least one of the first battery unit 123 and the second battery unit 124 has a remaining useful life above the respective threshold value.

When both the remaining life of the first battery unit 123 and the remaining life of the second battery unit 124 are below the respective threshold values, the combined rate at which power is drawn is reduced. Accordingly, the rate at which the electrical source 140 is charged by the charging circuit 130 is reduced. To account for this, the frequency at which energy is output to the patient is reduced. For example, the medical device 100 can increase the charging time between shocks. Alternatively or additionally, the amount of energy delivered to the patient in each shock can be reduced. In one example, the medical device 100 is configured to deliver shocks to the patient at approximately 200 joules, approximately 300 joules, and/or approximately 360 joules during normal operating conditions.

Figure 3:
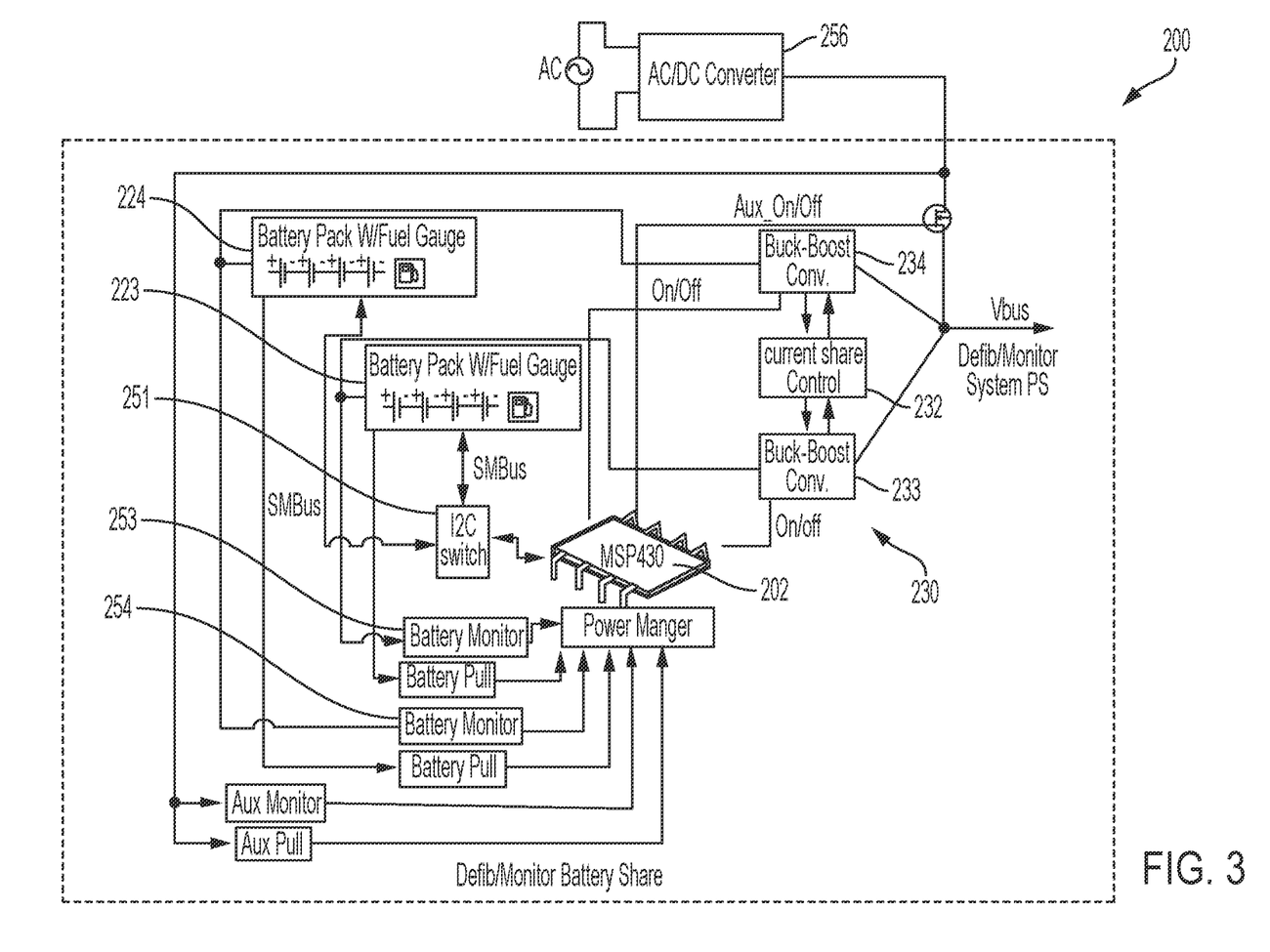
FIG. 3 is a simplified schematic of a medical device, according to an example implementation.

FIG. 3 illustrates a power circuit of a medical device 200. The medical device 200 is a device having a first operating mode with a high power usage and a second operating mode with a lower power usage. In some examples, the medical device 200 is an external defibrillator, such as the medical device 100 of FIGS. 1 and 2.

The medical device 200 has a controller 202 operably coupled to a first battery unit 223 and a second battery unit 224. The controller 202 includes a first battery monitor 253 for monitoring one or more parameters of the first battery unit 223 and a second battery monitor 254 for monitoring one or more parameters of the second battery unit 224. As discussed above, example parameters include remaining charge and/or parameters usable to determine the remaining useful life of the first battery unit 223 and the second battery unit 224.

The first battery unit 223 and the second battery unit 224 are selectively coupled to the medical device 200 by a charging circuit 230. The first battery unit 223 and the second battery unit 224 can be connected and disconnected from the medical device by the controller 202 through operation of switches 251.

The charging circuit 230 includes a first buck-boost converter 233, a second buck-boost converter 234, and a current share controller 232. The first battery unit 223 is operably coupled to the first buck-boost converter 233 such that the output voltage of the first battery unit 223 can be increased for use by the medical device 200. For example, the output voltage of the first battery unit 223 can be stepped up by the first buck-boost converter 233 to charge a high voltage electrical source.

Similarly, the second battery unit 224 is coupled to the second buck-boost converter 234 such that the output voltage of the second battery unit 224 can be increased for use by the medical device 200.

The current share controller 232 adjusts the rate at which power is drawn from the first battery unit 223 and the second battery unit 224. As discussed above with respect to the medical device 100, the rate at which power is drawn from the first battery unit 223 and the second battery unit 224 is adjusted by the controller based on the monitored parameters of the first and second battery units 223, 224.

The medical device 200 further includes an AC/DC converter 256. The AC/DC converter converts AC power to DC power. This enables the medical device 200 to be coupled to an external AC power supply, such as a standard wall outlet, in order to charge the first battery unit 223 and the second battery unit 224.

In operation, the medical device 200 operations substantially similarly to the medical device 100 described above. The controller 202 controls the operation of the medical device based on one or more of the monitored parameters of the first battery unit 223 and the second battery unit 224.

Figure 4:
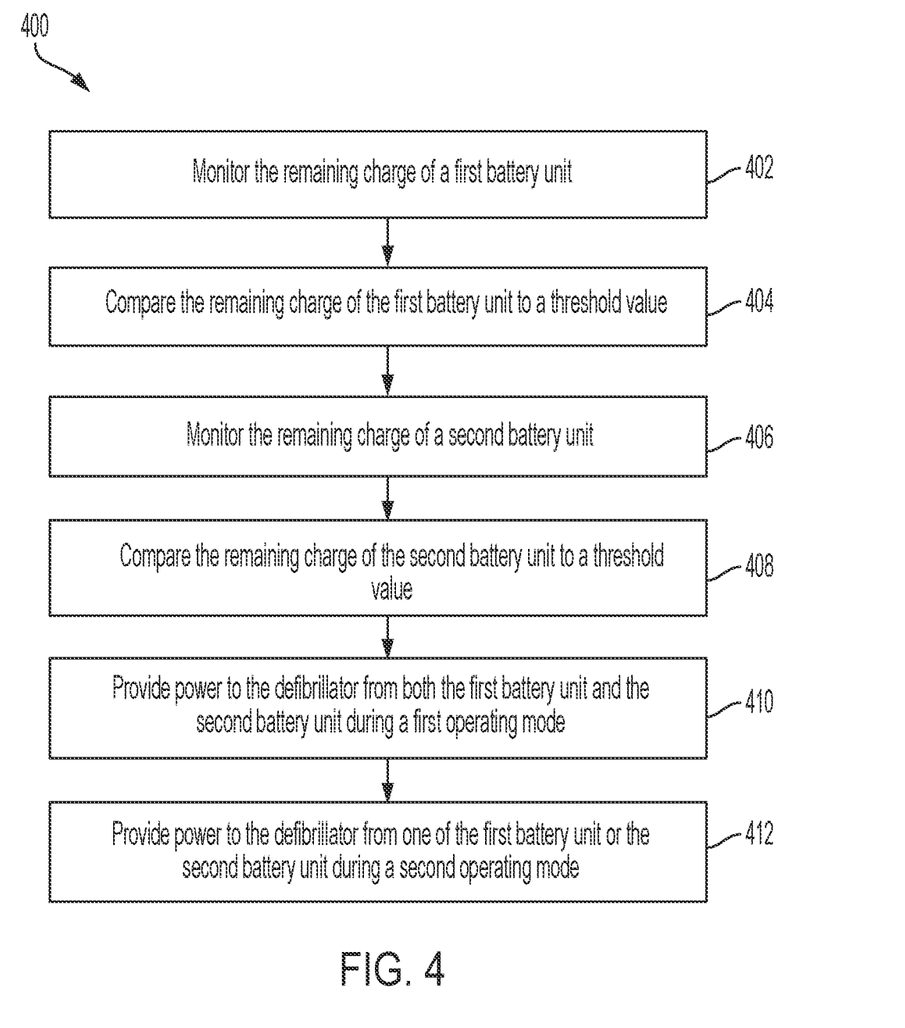
FIG. 4 is a flowchart illustrating a method of operating a medical device, according to an example implementation.

FIG. 4 illustrates a method 400 for operating a defibrillator. The method 400 can be performed by any of the medical devices 100, 200 described herein. As discussed above, the controller of a medical device can include computer readable memory. The computer readable memory stores executable instructions which, when executed, cause the controller to perform the method 400.

Step 402 comprises monitoring a remaining charge of a first battery unit. In step 404, the remaining charge of the first battery unit is compared to a stored threshold value.

Step 406 comprises monitoring a remaining charge of a second battery unit. In step 408, the remaining charge of the second battery unit is compared to a stored threshold value. As discussed above, the stored threshold values to which the remaining charge of the first battery unit and the second battery unit are compared can be the same threshold value or differing threshold values.

In step 410, power is provided to the defibrillator by both the first battery unit and the second battery unit while the defibrillator is in a first operating mode. Providing power to the defibrillator in the first operating mode comprises drawing power from the first battery unit at a first rate and drawing power from the second battery unit at a second rate.

In some examples, the method 400 further comprises adjusting the first rate and the second rate based on the remaining charge of the first battery unit and the remaining charge of the second battery unit. In some forms, adjusting the first rate and the second rate comprises adjusting a peak power draw of the first battery unit and a peak power draw of the second battery unit, respectively.

In step 412, power is provided to the defibrillator by one of the first battery unit or the second battery unit while the defibrillator is in a second operating mode. As discussed above, a controller determines which of the first battery unit or the second battery unit provides power to the defibrillator during the second operating mode based on the respective remaining charges. In one example, if both battery units have a remaining charge greater than the threshold value, power is provided to the defibrillator from the battery unit having the lower remaining charge. In an alternative implementation, power is provided to the defibrillator from the battery unit having the higher remaining charge.

In some forms, the method 400 further includes indicating the remaining charge of the first battery unit and the second battery unit via an indicator.

In some examples, the method 400 further includes providing power to the defibrillator from both the first battery unit and the second battery unit during the second operating mode. When the remaining charge of the first battery unit is below the threshold value and the remaining charge of the second battery unit is below the threshold value, power is provided to the defibrillator from both battery units. In some forms, the threshold value is between about 5% and about 50%. In one form, the threshold value is about 15%.

Figure 5:
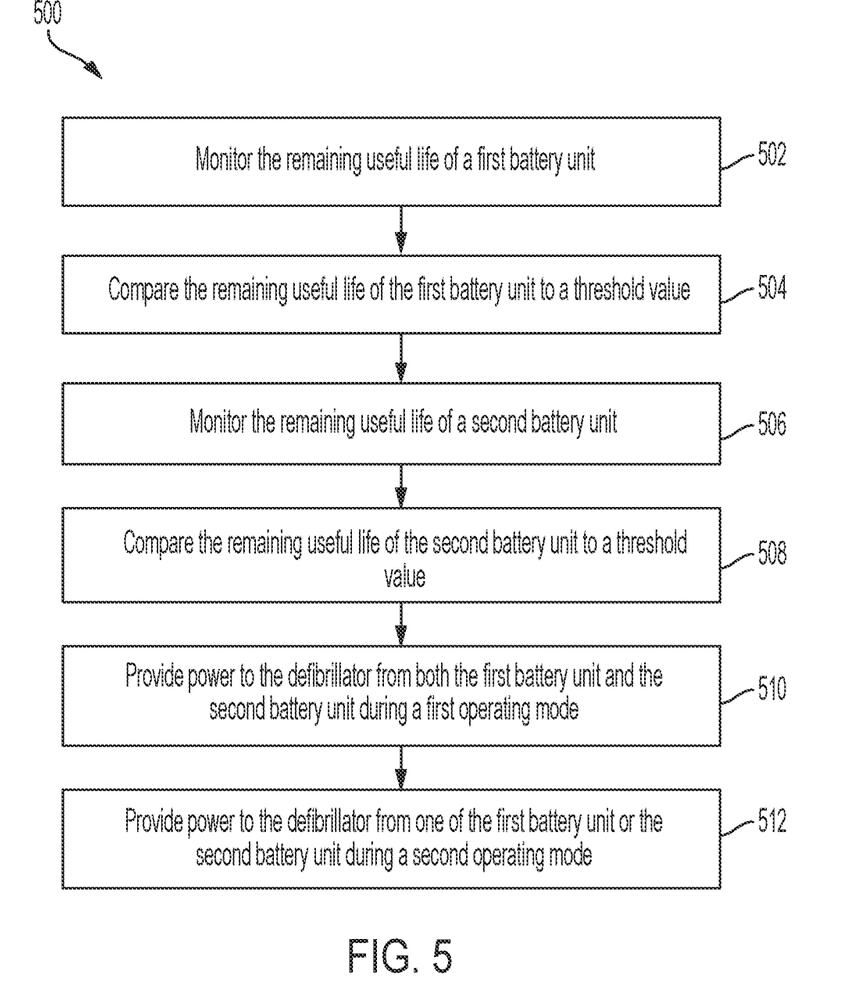
FIG. 5 is a flowchart illustrating another method of operating a medical device, according to an example implementation.

FIG. 5 illustrates a method 500 for operating a defibrillator. The method 500 can be performed by any of the medical devices 100, 200 described herein. As discussed above, the controller of a medical device can include computer readable memory. The computer readable memory stores executable instructions which, when executed, cause the controller to perform the method 500.

Step 502 comprises monitoring a remaining useful life of a first battery unit. In some forms, the remaining useful life of the first battery unit is determined based on one or more battery parameters. Example parameters usable to determine the remaining useful life of the first battery unit include absolute state of charge, battery current, battery voltage, charging current, charging voltage, discharge cycle count, date of battery first use, full charge capacity, relative state of charge, remaining capacity, run time to empty, temperature, or combinations thereof. In step 504, the remaining useful life of the first battery unit is compared to a stored threshold value.

Step 506 comprises monitoring a remaining useful life of a second battery unit. The remaining useful life of the second battery unit is determined using the same parameters described above. In step 508, the remaining useful life of the second battery unit is compared to a stored threshold value. As discussed above, the stored threshold values to which the remaining useful life of the first battery unit and the second battery unit are compared can be the same threshold value or differing threshold values.

In step 510, power is provided to the defibrillator by both the first battery unit and the second battery unit while the defibrillator is in a first operating mode. Providing power to the defibrillator in the first operating mode comprises drawing power from the first battery unit at a first rate and drawing power from the second battery unit at a second rate.

In some examples, the method 500 further comprises adjusting the first rate and the second rate based on the remaining useful life of the first battery unit and the remaining useful life of the second battery unit. In some forms, adjusting the first rate and the second rate comprises adjusting a peak power draw of the first battery unit and a peak power draw of the second battery unit, respectively.

In step 512, power is provided to the defibrillator by one of the first battery unit or the second battery unit while the defibrillator is in a second operating mode. As discussed above, a controller determines which of the first battery unit or the second battery unit provides power to the defibrillator during the second operating mode based on the respective remaining useful lives. In one example, the battery unit having the longer remaining useful life is used to power the defibrillator in the second operating mode. In an alternative embodiment, the battery unit having the shorter remaining useful life is used to power the defibrillator in the second operating mode.

In some forms, the method 500 further includes indicating to replace the first battery unit when the remaining useful life of the first battery unit is below the threshold value. Similarly, the method 500 further includes indicating to replace the second battery unit when the remaining useful life of the second battery unit is below the threshold value.

In some examples, the method 500 further includes providing power to the defibrillator from both the first battery unit and the second battery unit during the second operating mode. When the remaining useful life of the first battery unit is below the threshold value and the remaining useful life of the second battery unit is below the threshold value, power is provided to the defibrillator from both battery units. In some forms, the threshold value is between about 5% and about 50% of the original operational life. In one form, the threshold value is between about 5% and about 15% of the original operational life.

Various additional alterations and changes beyond those already mentioned herein can be made to the above-described implementations. This disclosure is presented for illustrative purposes and should not be interpreted as an exhaustive description of all implementations or to limit the scope of the claims to the specific elements illustrated or described in connection with these implementations. For example, and without limitation, any individual element(s) of the described implementations may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A defibrillator assembly comprising:
a defibrillator having a first operating mode for delivering a high energy output to a patient and a second operating mode for monitoring the patient;
a first battery unit operably coupled to the defibrillator;
a second battery unit operably coupled to the defibrillator;
a battery charge monitor configured to determine a remaining charge of the first battery unit and the second battery unit; and
a controller having a processor, the controller configured to:
cause the defibrillator to use only one of the first battery unit and the second battery unit during the second operating mode,
cause the defibrillator to use both the first battery unit and the second battery unit during the first operating mode, and
cause the first battery unit and the second battery unit to provide power to the defibrillator proportional to their respective remaining charge during the first operating mode.

2. The defibrillator assembly of claim 1, wherein the first battery unit is detachable from the defibrillator.

3. The defibrillator assembly of claim 1, further comprising an indicator configured to indicate a charge status of the at least one of the first battery unit or the second battery unit.

4. The defibrillator assembly of claim 3, wherein the indicator is configured to indicate a remaining operation time of the defibrillator.

5. The defibrillator assembly of claim 1, wherein the controller is configured to cause the defibrillator to use the one of the first battery unit and the second battery unit having a lower remaining charge during the second operating mode.

6. The defibrillator assembly of claim 1, wherein the controller is configured to cause the defibrillator to use the one of the first battery unit and the second battery unit having a higher remaining charge during the second operating mode.

7. The defibrillator assembly of claim 1, wherein:
the battery charge monitor is configured to compare the remaining charge of the first battery unit to a threshold value and compare the remaining charge of the second battery unit to the threshold value, and
when one of the first battery unit and the second battery unit has a remaining charge above the threshold value and the other of the first battery unit and the second battery unit has a remaining charge below the threshold value, the controller is configured to cause the defibrillator to use only the one of the first battery unit and the second battery unit having a remaining charge above the threshold value during the first operating mode.

8. The defibrillator assembly of claim 1, further comprising:
a charging circuit operably coupled to the first battery unit and the second battery unit; and
an electrical source operably coupled to the charging circuit,
wherein the charging circuit is configured to charge the electrical source with power from the first battery unit and the second battery unit during the first operating mode.

9. A medical device comprising:
a first battery unit;
a second battery unit;
a battery charge monitor configured to determine the remaining charge of the first battery unit and the second battery unit; and
a controller having a processor, the controller configured to:
cause the medical device to use only one of the first battery unit and the second battery unit during a low power operating mode,
cause the medical device to use both the first battery unit and the second battery unit during a high power operating mode, and
cause the first battery unit and the second battery unit to provide power to the medical device proportional to their respective remaining charge during the high power operating mode.

10. The medical device of claim 9, further comprising an indicator configured to indicate a charge status of the first battery unit and the second battery unit.

11. The medical device of claim 9, wherein the controller is configured to cause the medical device to use the one of the first battery unit and the second battery unit having a lower remaining charge during the low power operating mode.

12. The medical device of claim 9, wherein the controller is configured to cause the medical device to use the one of the first battery unit and the second battery unit having a higher remaining charge during the low power operating mode.

13. A defibrillator assembly comprising:
a defibrillator having a first operating mode for delivering a high energy output to a patient;
a first battery unit operably coupled to the defibrillator;
a second battery unit operably coupled to the defibrillator;

a battery charge monitor configured to determine the remaining charge of the first battery unit and the second battery unit; and a controller having a processor, the controller configured to:

cause the first battery unit and the second battery unit to provide power to the medical device proportional to their respective remaining charge during the first operating mode, determine a remaining useful life of the first battery unit and the second battery unit, and cause the defibrillator to use only a one of the first battery unit and the second battery unit having a longer remaining useful life during a second operating mode.

14. The defibrillator assembly of claim 13, wherein the controller is configured to cause the defibrillator to use both the first battery unit and the second battery unit during the first operating mode.

15. The defibrillator assembly of claim 13, wherein the first operating mode has a peak power draw on the first battery unit, and wherein the controller is configured to adjust the peak power draw based on the remaining useful life of the first battery unit.

* * * * *